(12) United States Patent
Huang et al.

(10) Patent No.: US 12,365,641 B2
(45) Date of Patent: Jul. 22, 2025

(54) METHOD FOR PREPARING 1,3-PROPANEDIOL WITH HIGH SPACE-TIME YIELD AND HIGH CONCENTRATION

(71) Applicant: LANZHOU INSTITUTE OF CHEMICAL PHYSICS, CHINESE ACADEMY OF SCIENCES, Lanzhou (CN)

(72) Inventors: Zhiwei Huang, Lanzhou (CN); Xiaolan Yao, Lanzhou (CN); Xuemei Li, Lanzhou (CN); Jian Yang, Lanzhou (CN); Chungu Xia, Lanzhou (CN)

(73) Assignee: LANZHOU INSTITUTE OF CHEMICAL PHYSICS, CHINESE ACADEMY OF SCIENCES, Lanzhou (CN)

( * ) Notice: Subject to any disclaimer, the term of this patent is extended or adjusted under 35 U.S.C. 154(b) by 0 days.

(21) Appl. No.: 18/893,901

(22) Filed: Sep. 23, 2024

(65) Prior Publication Data

US 2025/0011262 A1 Jan. 9, 2025

(30) Foreign Application Priority Data

Nov. 7, 2023 (CN) .......................... 202311470918.8

(51) Int. Cl.
*C07C 29/149* (2006.01)
*B01J 21/08* (2006.01)
(Continued)

(52) U.S. Cl.
CPC ............. *C07C 29/149* (2013.01); *B01J 21/08* (2013.01); *B01J 23/80* (2013.01); *B01J 23/825* (2013.01);
(Continued)

(58) Field of Classification Search
CPC .................................................. C07C 29/149
See application file for complete search history.

(56) References Cited

U.S. PATENT DOCUMENTS 5,723,389 A 3/1998 Slaugh et al.
5,770,776 A 6/1998 Powell et al.
(Continued)

FOREIGN PATENT DOCUMENTS

CN 103804143 A 5/2014
CN 116689032 A 9/2023
(Continued)

OTHER PUBLICATIONS

CN116689032A, Machine translation, Sep. 5, 2023, pp. 1-11 (Year: 2023).*

*Primary Examiner* — Medhanit W Bahta (57) ABSTRACT

A method for preparing 1,3-propanediol with a high space-time yield, in which A methyl 3-hydroxypropionate solution is pumped into a tubular fixed-bed reactor loaded with a surface modifier-coated nano-Cu-based catalyst for continuous hydrogenation to obtain a reaction mixture, where the catalyst includes Cu as active component, a metal oxide $XO_{n/2}$ as additive and a $SiO_2$—$SnO_2$ composite carrier. The reaction mixture is subjected to rectification to separate light components from heavy components, where the light components include methanol, n-propanol, methyl propionate, methyl 3-hydroxypropionate and 1,3-propanediol, and the heavy components include 1,3-propanediol mono-propionate and 1,3-propanediol mono-3-hydroxypropionate. The heavy components are fed back to the tubular fixed-bed reactor for secondary hydrogenation, and the light components are separated to obtain 1,3-propanediol.

5 Claims, 3 Drawing Sheets (51) Int. Cl.
  *B01J 23/80* (2006.01)
  *B01J 23/825* (2006.01)
  *B01J 23/835* (2006.01)

(52) U.S. Cl.
  CPC .......... *B01J 23/835* (2013.01); *B01J 2523/36* (2013.01); *B01J 2523/3712* (2013.01); *B01J 2523/3768* (2013.01)

(56)  References Cited

U.S. PATENT DOCUMENTS

| | | |
|---|---|---|
| 5,777,182 A | 7/1998 | Powell et al. |
| 6,140,543 A | 10/2000 | Brossmer et al. |
| 6,191,321 B1 | 2/2001 | Forschner et al. |
| 6,232,511 B1 | 5/2001 | Haas et al. |
| 6,600,065 B2 | 7/2003 | Cho et al. |
| 6,617,478 B2 | 9/2003 | Lee et al. |

FOREIGN PATENT DOCUMENTS

| | | |
|---|---|---|
| DE | 3734764 A1 | 5/1989 |
| EP | 0361082 A2 | 4/1990 |
| EP | 1211234 A2 | 6/2002 |
| KR | 20020042397 A | 6/2002 |

\* cited by examiner

METHOD FOR PREPARING 1,3-PROPANEDIOL WITH HIGH SPACE-TIME YIELD AND HIGH CONCENTRATION

CROSS-REFERENCE TO RELATED APPLICATIONS

This application claims the benefit of priority from Chinese Patent Application No. 202311470918.8, filed on Nov. 7, 2023. The content of the aforementioned application, including any intervening amendments thereto, is incorporated herein by reference in its entirety.

TECHNICAL FIELD

This application relates to fine chemical engineering, and more specifically to a method for preparing 1,3-propanediol with high space-time yield and high concentration.

BACKGROUND 1,3-propanediol is an important chemical raw material and a basic monomer material for many polymers. It can be used as a solvent, antifreeze or protective agent, fine chemical raw material, etc. It can also be used for the synthesis of medicine and organic intermediates.

At present, the main production routes of 1,3-propanediol are introduced as follows. (1) Ethylene oxide method proposed by Shell USA Inc., in which ethylene oxide is subjected to hydroformylation reaction to obtain 3-hydroxypropanal, followed by hydrogenation to obtain 1,3-propanediol (see U.S. Patent Publication Nos. 5770776A, 5777182A, and 5723389A). (2) Acrolein hydration-hydrogenation method proposed by Degussa (German), in which acrolein experiences hydration to obtain 3-hydroxypropanal, followed by hydrogenation to obtain 1,3-propanediol (see U.S. Patent Publication Nos. 6140543A and 6232511B1). (3) Bio-fermentation proposed by DuPont Company (US), which employs microorganisms to convert glucose (from cereal starch, e.g., corn starch) to 1,3-propanediol (see German Patent Publication No. 3734764A1 and European Patent Publication No. 361082A2). The first two methods both involves hydrogenation of the intermediate 3-hydroxypropanal, however, this intermediate is unstable, and is prone to polymerization to generate by-products, such as oligomers and acetal, so that it is difficult to yield the polyester-grade product. Furthermore, the concentration of hydrogenation raw material is low (usually <20 wt. %), and a large amount of water is used as solvent, which leads to high energy consumption for separation. Regarding the microbiological fermentation method, it has high requirements for bacterial strains, low product concentration (usually <10 wt. %), complex separation process, and poor production efficiency.

To solve problems in the synthesis route of 1,3-propanediol with 3-hydroxypropanal as the intermediate, David-Samsung Company adopts an ethylene oxide hydroesterification method, in which ethylene oxide, carbon monoxide and alcohol compounds are subjected to hydroesterification reaction to generate 3-hydroxypropionate, and the ester groups in the 3-hydroxypropionate are hydrogenated the to obtain 1,3-propanediol (see U.S. Patent Publication No. 6191321B1). In the ethylene oxide hydroesterification method, the intermediate (3-hydroxypropionate) has a higher stability, and the hydrogenated product is easy to reach polymerization grade. Hence, this method is promising for industrial production of 1,3-propanediol. It should be noted that the 3-hydroxyl group of 3-hydroxypropionate is easy to be removed by the formation of water. Therefore, it is difficult to achieve high selectivity and high yield with conventional commercial hydrogenation catalysts, such as Cu—Cr catalysts, Raney-Ni, Pd/C and Pt/C, etc. To improve the hydrogenation activity and selectivity of 3-hydroxypropionate, U.S. Patent Publications Nos. U.S. Pat. Nos. 6,600,065 and 6,617,478 proposed $CuO$—$SiO_2$ and $CuO$—$SiO_2$ modified with $MnO_2$ as catalysts for the hydrogenation of methyl 3-hydroxypropionate to prepare 1,3-propanediol, with a conversion rate up to 90% or more and a selectivity rate up to 85%. However, these catalysts show high activity only for low-concentration raw materials with a low space-time yield of 1,3-propanediol product (<0.05 g/(g·h)).

Chinese Patent Publication No. 103804143B disclosed a process for preparing 1,3-propanediol by hydrogenating high-concentration methyl 3-hydroxypropionate. Specifically, high-concentration (50-100 wt. %) methyl 3-hydroxypropionate was used as raw material, which experienced two-stage fixed-bed hydrogenation, two-stage separation, and rectification to achieve the high conversion of methyl 3-hydroxypropionate and high yield of 1,3-propanediol. Nevertheless, the activity of the $CuMnZnNi/SiO_2$ catalyst used in this process is not high enough, leading to a low one-way space-time yield (<0.1 g/(g·h)) when catalyzing the hydrogenation of high-concentration methyl 3-hydroxypropionate. Moreover, as an important index reflecting the catalyst performance, the lifetime stability is not mentioned. In addition, after separating light components from the first hydrogenated product, it is required to further hydrogenate the components containing 1,3-propanediol and 1,3-propanediol monopropionate at a high pressure to reach a high 1,3-propanediol yield, that is, two-stage high-pressure fixed-bed hydrogenation is required, resulting in a long reaction process and a high equipment investment.

Chinese Patent Publication No. 116689032A disclosed a catalyst for selective hydrogenation of a hydroxyester and a preparation method thereof. The activity, selectivity, and stability of copper-silicon nano-catalysts are significantly improved through synergistic effect of multifunctional additives and surface alkaline additives. The catalytic hydrogenation of a 20 wt. % methyl 3-hydroxypropionate solution (dissolved in methanol) was continuously performed in a tubular fixed-bed reactor at a weight hourly space velocity of 0.2 $h^{-1}$, with the reaction conversion rate and the reaction selectivity both reaching 90% or more, and the long-term stability reaching 500 h. However, the catalytic activity is not high enough. The conversion rate of the 20 wt. % methyl 3-hydroxypropionate solution is only slightly above 90%, and the long-term stability of the catalyst is not satisfactory, with the hydrogenation catalyzing performance declined after 500 h. In addition, a large amount of methanol is added as the solvent to improve the selectivity of the target product, which increases the energy consumption for the separation of 1,3-propanediol, and also may damage the catalyst structure, affecting the long-term stability of the catalyst.

In summary, although the existing technology has improved the hydrogeneration conversion rate and selectivity of the preparation of 1,3-propanediol from 3-hydroxypropionate by introducing various additives into catalysts and optimizing reaction conditions, there are still some shortcomings such as low reactant concentration, low space-time yield of the target product, and poor long-term stability of the catalysts, which restrict the development and application of the catalytic hydrogenation of 3-hydroxypropionate to produce 1,3-propanediol.

SUMMARY

An objective of the present disclosure is to provide a method for preparing 1,3-propanediol with high space-time yield and high concentration to overcome the problems in the prior art such as low reactant concentration, poor space-time yield of the target product and poor long-term stability of the catalysts.

A method for preparing 1,3-propanediol, comprising:

pumping, by a feed pump, methyl 3-hydroxypropionate solution into a tubular fixed-bed reactor for hydrogenation to obtain a reaction mixture, wherein the tubular fixed-bed reactor is loaded with a surface modifier-coated nano-Cu-based catalyst;

subjecting the reaction mixture to rectification to separate light components from heavy components, wherein the light components comprise methanol, n-propanol, methyl propionate, methyl 3-hydroxypropionate and 1,3-propanediol; and the heavy components comprise 1,3-propanediol mono-propionate and 1,3-propanediol mono-3-hydroxypropionate; and feeding the heavy components back to the tubular fixed-bed reactor for secondary hydrogenation; and subjecting the light components to separation to collect 1,3-propanediol;

wherein the surface modifier is selected from the group consisting of an organic aluminum salt, an organic zirconium salt and a combination thereof;

the nano-Cu-based catalyst comprises an active component, an additive component, a carrier and a surface modifier, wherein the active component is Cu, and the additive component is a metal oxide of $XO_{n/2}$;

the carrier is a complex of $SiO_2$ and $SnO_2$; and

X is selected from the group consisting of Zn, Ga, Ge, In, Y, Ce, Ho and a combination thereof;

the surface modifier-coated nano Cu-based catalysts comprises 30-70 wt. % of the active component CuO, 1-15 wt. % of the additive component $XO_{n/2}$, 15-60 wt. % of $SiO_2$, 1-5 wt. % of $SnO_2$, and 0.3-9.0 wt. % of the surface modifier;

the surface modifier-coated nano-Cu-based catalyst is prepared through steps of:

(1) mixing a copper precursor and an $X^{n+}$ metal precursor with a preset weight ratio to form a mixed aqueous solution A with a molar concentration of 0.1-1 mol/L;

(2) preparing a base solution B with a molar concentration of 0.5-5 mol/L as precipitant;

(3) adding a sol or nano-powder of $SiO_2$ and $SnO_2$ to a cooled aqueous solution containing an organic polyol to form a carrier mixture solution;

(4) simultaneously adding the mixed aqueous solution A and the base solution B to the carrier mixture solution under stirring for co-precipitation to form a slurry, wherein a pH of the slurry is kept at 10-12 during the co-precipitation;

(5) after the co-precipitation is completed, heating the slurry to 80-100° C. for high-temperature aging for 2-24 h, followed by filtration, washing, atmospheric-pressure drying, and calcination to obtain a nano-Cu-based catalyst precursor;

(6) subjecting the nano-Cu-based catalyst precursor obtained from step (5) to impregnation with a surface modifier, drying and calcination to obtain a catalyst powder; and (7) subjecting the catalyst powder obtained from step (6) to pressing-sieving or extrusion, and reduction activation to obtain the surface modifier-coated nano-Cu-based catalyst;

wherein in step (1), the copper precursor is a soluble copper nitrate or sulfate, the $X^{n+}$ metal precursor is a soluble metal nitrate or sulfate;

in step (2), the base solution B is one or two of sodium hydroxide, sodium bicarbonate, sodium carbonate, ammonium carbonate, ammonium bicarbonate and ammonia;

in step (3), the organic polyol is selected from the group consisting of ethylene glycol, 1,2-propanediol, glycerol, glucose, sucrose, sorbitol and cyclodextrin;

in step (4), the co-precipitation is performed at a temperature ranging from −10° C. to 10° C.

in steps (5)-(6), the drying is performed at 90-120° C. under an atmospheric pressure, and the calcination is performed at 400-700° C.;

in step (6), the surface modifier is one of aluminum isopropoxide, aluminum sec-butoxide, zirconium n-propoxide and zirconium n-butoxide, or a combination of one of aluminum isopropoxide and aluminum sec-butoxide and one of zirconium n-propoxide and zirconium n-butoxide;

operation parameters of a bed layer of the tubular fixed-bed reactor are as follows: the temperature at the constant-temperature section is 160-200° C., the pressure is 8-12 MPa, the concentration of the methyl 3-hydroxypropionate solution is 90-99 wt. %, the hydrogen-to-ester molar ratio is 30-200:1, and the weight hourly space velocity is 0.2-0.6 $h^{-1}$; and the purity of 1,3-propanediol is up to 99.9 wt. % after purified by vacuum distillation.

Compared with the prior art, the present disclosure has at least the following advantages.

(1) During the catalyst preparation provided herein, low-temperature precipitation performed in the co-presence of a precipitant and an organic polyol and high-temperature aging are adopted for subsequent treatment, which can effectively avoid the aggregation of catalyst particles caused by instantaneous heat release during the precipitation process, improve the dispersion state of the active metal component, promote the generation of highly-dispersed copper phyllosilicate species, and optimize the $Cu^+/Cu^0$ ratio, thereby significantly enhancing the hydrogenation activity and selectivity of the catalyst.

(2) In the present disclosure, the catalyst precursor is coated with a surface modifier for modification. In this case, a large number of defective sites are formed on the catalyst surface, promoting the adsorption and activation of the ester carbonyl group, thereby improving the hydrogenation activity of the catalyst. Moreover, a protective shell layer is formed on the catalyst, which can effectively inhibit the sintering of the active metal and the loss of the silica carrier, thereby significantly improving the catalyst stability.

(3) High-concentration methyl 3-hydroxypropionate is used as raw material, which reduces the energy consumption of solvent separation and the damage to the catalyst structure, thus significantly prolonging the service life of the catalyst.

(4) The heavy components separated by the distillation are directly fed into the next batch of raw material for further hydrogenation to generate 1,3-propanediol, which can reduce the equipment investment and production costs, and improve the economic efficiency.

(5) The 1,3-propanediol separated from the rectification tower has a high purity, up to 99.9%, which satisfies the production requirements of polyesters.

(6) The catalyst has high catalytic hydrogenation activity and outstanding stability, with a single-pass conversion rate of methyl 3-hydroxypropionate exceeding 99 wt. %, the 1,3-propanediol yield more than 84 mol %, and a long-term stability more than 1,000 h, exhibiting great industrial application potential.

(7) By means of the catalyst designed herein, the preparation method provided herein has excellent space-time yield of 1,3-propanediol, thereby facilitating enhancing the production efficiency and improving the economic efficiency.

DETAILED DESCRIPTION OF EMBODIMENTS

To make the objects, technical solutions and advantages of the present disclosure clearer and more understandable, the present disclosure will be described in further detail below with reference to embodiments. It should be understood that the specific embodiments described herein are only for explaining the present disclosure and are not intended to limit the present disclosure.

The application principle of the present disclosure will be further described below with reference to the accompanying drawings and specific embodiments.

In the following description, 3-HPM refers to methyl 3-hydroxypropionate, and 1,3-PDO refers to 1,3-propanediol.

Example 1

1. Preparation of a Surface Modifier-Coated Nano-Cu-Based Catalyst 48.32 g of copper nitrate, 4.39 g of zinc nitrate, 2.1 g of holmium nitrate and 1.95 g of indium nitrate were dissolved in 441 mL of deionized water to form a mixed nitrate solution. 32 g of silica sol, 1.5 g of $SnO_2$ nano-powder, 16 mL of ionized water and 2.34 g of ethylene glycol were added to a reactor, cooled to 5° C. and kept at 5° C. to form a carrier mixture solution. The mixed nitrate solution and a 5 mol/L sodium hydroxide solution were simultaneously dropwise added into the carrier mixture solution under stirring for precipitation, during which the reaction solution was kept at pH 12. After the precipitation was completed, the reaction solution was heated to 90° C. for aging for 6 h, and filtrated to collect a filter cake, which was rinsed with deionized water to neutral, dried at 110° C. for 24 h and calcinated at 500° C. for 4 h to obtain a nano-Cu-based catalyst precursor $53CuO4ZnO3Ho_2O_33In_2O_3/32SiO_25SnO_2$. 0.41 g of aluminum sec-butoxide was dissolved in sec-butanol with calculated amount, to which 10 g of the above catalyst precursor was added, impregnated at room temperature for 2 h, dried at 110° C. for 12 h, and calcinated at 600° C. for 4 h to obtain the surface modifier-coated nano-Cu-based catalyst ($53CuO4ZnO3Ho_2O_33In_2O_3/32SiO_25SnO_2@1\% Al_2O_3$).

Figure 1:
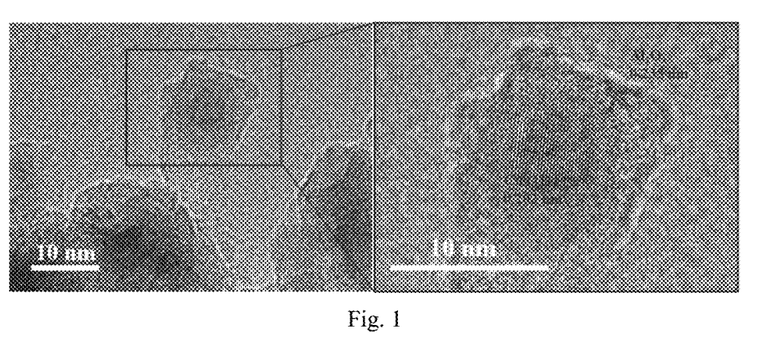
FIG. 1 is a high-resolution transmission electron microscope (TEM) image of a catalyst provided in Example 1 of the present disclosure.

The transmission electron microscope (TEM) image of the prepared catalyst was shown in FIG. 1, which showed that the catalyst had an obvious core-shell structure after the reductive activation, and the active component copper was coated by the surface modifier.

Figure 2:
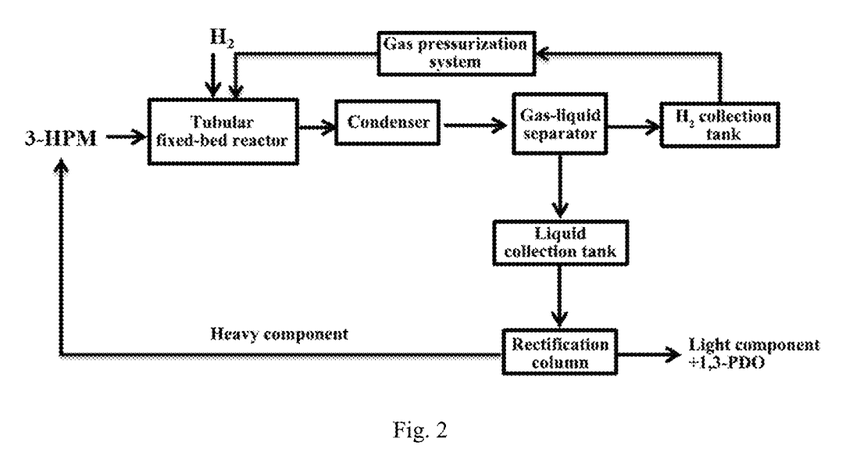
FIG. 2 is a flow chart of a method for preparing 1,3-propanediol with a high space-time yield according to an embodiment of the present disclosure.

2. Preparation of 1,3-Propanediol (as Shown in FIG. 2)

(1) 8 g of the surface modifier-coated nano-Cu-based catalyst was pressed, ground, and sieved to obtain 20-40 mesh particles, which were loaded into a constant-temperature section of a tubular fixed-bed reactor. The rest part of the tubular fixed-bed reactor was filled with inert SiC. The catalyst was subjected to reductive activation in a mixed atmosphere of 20% $H_2$ and 80% $N_2$ at an atmospheric pressure and 250° C. for 8 h. After cooled down to 170° C., the tubular fixed-bed reactor was pressurized to 9 MPa with high-purity $H_2$.

(2) A methyl 3-hydroxypropionate solution with a concentration of 99 wt. % was pumped into the tubular fixed-bed reactor via a feed pump and hydrogenated at 170° C. under hydrogen gas pressure (9 MPa $H_2$) to obtain a hydrogenated product, where a mole ratio of hydrogen to methyl 3-hydroxypropionate was 120:1, and a weight hourly space velocity was 0.25 $h^{-1}$.

(3) The hydrogenated product was cooled by a condenser, and then entered a gas-liquid separator, where the separated liquid was collected into a liquid collection tank, and the gas was collected into a $H_2$ collection tank to be pressurized by the gas pressurization system for reuse.

(4) The liquid in the liquid collection tank was fed into a rectification column to separate light components from heavy components, where the light components included methanol, n-propanol, methyl propionate, methyl 3-hydroxypropionate and the target product 1,3-propanediol, and the heavy components included 1,3-propanediol mono-propionate and 1,3-propanediol mono-3-hydroxypropionate. The heavy components were mixed with the next batch of raw material in a concentration of 5 wt. % for secondary hydrogenation.

3. Evaluation of Catalyst Performance

After the hydrogenation reaction was performed for 60 h, the hydrogenated product obtained from step (2) was analyzed qualitatively and quantitatively by gas chromatography.

Figure 3:
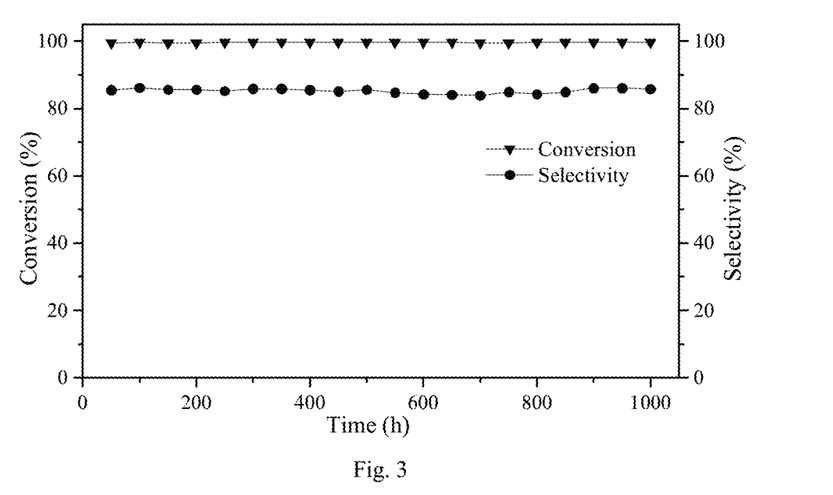
FIG. 3 shows evaluation results of hydrogenation stability using a fixed-bed reactor loaded with the catalyst provided in Example 1 of the present disclosure.

FIG. 3 showed that the conversion rate of methyl 3-hydroxypropionate was 99.5%, the 1,3-propanediol selectivity was 85.0%, and the catalyst performance remained stable in 1000 h. These results demonstrated that the preparation method of the present disclosure had a high space-time yield of 1,3-propanediol (up to 0.154 g/(g·h)), and the catalyst provided by the present disclosure has an excellent long-term stability. High-purity of 1,3-propanediol (99.9%) could be obtained by distillation of the light components.

Example 2

1. Preparation of a Surface Modifier-Coated Cu-Based Nano-Catalyst 27.35 g of copper nitrate, 1.4 g of holmium nitrate and 4.09 g of gallium nitrate were dissolved in 1228 mL of deionized water to form a mixed nitrate solution. 18 g of $SiO_2$ nano-powder, 0.9 g of $SnO_2$ nano-powder, 50 mL of ionized water and 8.5 g of sucrose were added to a reactor, cooled to −5° C. and kept at −5° C. to form a carrier mixture solution. The mixed nitrate solution and a 0.5 mol/L sodium hydroxide solution were simultaneously dropwise added into the carrier mixture solution under stirring for precipitation, during which the reaction solution was kept at pH 12. After the precipitation was completed, the reaction solution was heated to 100° C. for aging for 2 h, and filtrated to collect a filter cake, which was rinsed with deionized water to neutral, dried at 100° C. for 24 h and calcinated at 500° C. for 4 h to obtain a nano-Cu-based catalyst precursor $30CuO2Ho_2O_35Ga_2O_3/60SiO_23SnO_2$. 0.78 g of zirconium tetra-n-propanol and 0.42 g of aluminum sec-butoxide were dissolved in sec-butanol with calculated amount, to which 10 g of the above catalyst precursor powder was added, impregnated at room temperature for 2 h, dried at 110° C. for 12 h, and calcinated at 600° C. for 4 h to obtain the surface modifier-coated nano-Cu-based catalyst ($30CuO2Ho_2O_35Ga_2O_3/60SiO_23SnO_2@2\%$ $Al_2O_3@1\%$ $ZrO_2$).

2. Preparation of 1,3-Propanediol

The preparation of 1,3-propanediol in Example 2 was basically the same as that in Example 1, except that in Example 2, the hydrogenation was performed at 180° C., and the ratio of hydrogen to methyl 3-hydroxypropionate was 200:1.

3. Evaluation of Catalyst

After the hydrogenation reaction was performed for 60 h, the hydrogenated product was analyzed qualitatively and quantitatively by gas chromatography, and results were as follows: the conversion rate of methyl 3-hydroxypropionate was 98.6%, the 1,3-propanediol selectivity was 81.2%, and a space-time yield of 1,3-propanediol was 0.146 g/(g·h)).

Example 3

1. Preparation of a Surface Modifier-Coated Cu-Based Nano-Catalyst 63.28 g of copper nitrate, 7.68 g of zinc nitrate, 1.95 g of indium nitrate, 0.76 g of cerium nitrate and 2.46 g of gallium nitrate were dissolved in 600 mL of deionized water to form a mixed nitrate solution. 15 g of silica sol, 0.3 g of $SnO_2$ nano-powder, 7.5 ml of ionized water and 15 g of ethylene glycol were added to a reactor, cooled to 5° C. and kept at 5° C. to form a carrier mixture solution. The mixed nitrate solution and a 3 mol/L sodium hydroxide solution were simultaneously dropwise added into the carrier mixture solution under stirring for precipitation, during which the reaction solution was kept at pH 10. After the precipitation was completed, the reaction solution was heated to 80° C. for aging for 24 h, filtrated to collect a filter cake, which was rinsed with deionized water to neutral, dried at 90° C. for 24 h and calcinated at 400° C. for 4 h to obtain a nano-Cu-based catalyst precursor $70CuO7ZnO1Ce_2O_33In_2O_33GeO_2/15SiO_21SnO_2$. 3.69 g of aluminum sec-butoxide was dissolved in sec-butanol with calculated amount, to which 10 g of the above catalyst precursor powder was added, impregnated at room temperature for 3 h, dried at 110° C. for 12 h, and calcinated at 600° C. for 4 h to obtain the surface modifier-coated nano-Cu-based catalyst ($70CuO7ZnO1Ce_2O_33In_2O_33GeO_2/15SiO_21SnO_2@9\%$ $Al_2O_3$).

2. Preparation of 1,3-propanediol

The preparation of 1,3-propanediol in Example 3 was basically the same as that in Example 1, except that in Example 3, the hydrogenation was performed at 165° C., and a concentration of methyl 3-hydroxypropionate raw material was 90%.

3. Evaluation of Catalyst

After the hydrogenation reaction was performed for 60 h, the hydrogenated product was analyzed qualitatively and quantitatively by gas chromatography, and results were as follows: the conversion rate of methyl 3-hydroxypropionate was 99.8%, the selectivity to 1,3-propanediol was 85.6%, and a space-time yield of 1,3-propanediol was 0.156 g/(g·h)).

Example 4

1. Preparation of a Surface Modifier-Coated Cu-Based Nano-Catalyst 51.82 g of copper sulfate, 6.36 g of zinc sulfate and 7.37 g of gallium nitrate were dissolved in 488 mL of deionized water to form a mixed sulfate solution. 26 g of silica sol, 1.2 g of $SnO_2$ nano-powder, 13 mL of ionized water and 2.0 g of ethylene glycol were added to a reactor, cooled to −10° C. and kept at −10° C. to form a carrier mixture solution. The mixed sulfate solution and a 4 mol/L mixture solution of sodium carbonate and sodium bicarbonate were simultaneously dropwise added into the carrier mixture solution under stirring for precipitation, during which the reaction solution was kept at pH 10. After the precipitation was completed, the reaction solution was heated to 90° C. for aging for 4 h, and filtrated to collect a filter cake, which was rinsed with deionized water to neutral, dried at 110° C. for 24 h and calcinated at 500° C. for 4 h to obtain a nano-Cu-based catalyst precursor $55CuO6ZnO9Ga_2O_3/26SiO_24SnO_2$. 0.21 g of aluminum sec-butoxide was dissolved in sec-butanol with calculated amount, to which 10 g of the above catalyst precursor powder was added, impregnated at room temperature for 3 h, dried at 110° C. for 12 h, and calcinated at 700° C. for 4 h to obtain the surface modifier-coated nano-Cu-based catalyst ($55CuO6ZnO9Ga_2O_3/26SiO_24SnO_2@0.3\%$ $Al_2O_3$).

2. Preparation of 1,3-Propanediol

The preparation of 1,3-propanediol in Example 4 was basically the same as that in Example 1, except that in Example 4, the hydrogenation was performed at 200° C., and a weight hourly space velocity was 0.6 $h^{-1}$.

3. Evaluation of Catalyst Performance

After the hydrogenation reaction was performed for 60 h, the hydrogenated product was analyzed qualitatively and quantitatively by gas chromatography, and results were as follows: the conversion rate of methyl 3-hydroxypropionate was 99.0%, the 1,3-propanediol selectivity was 80.3%, and a space-time yield of 1,3-propanediol was 0.157 g/(g·h)).

Example 5

1. Preparation of a Surface Modifier-Coated Cu-Based Nano-Catalyst 41.03 g of copper nitrate, 3.29 g of zinc nitrate, 2.8 g of holmium nitrate and 1.02 g of yttrium nitrate were dissolved in 185 mL of deionized water to form a mixed nitrate solution. 42 g of silica sol, 1.5 g of $SnO_2$ nano-powder, 21 mL of ionized water and 2.5 g of ethylene glycol were added to a reactor, cooled to 5° C. and kept at 5° C. to form a carrier mixture solution. The mixed nitrate solution and a 3 mol/L sodium hydroxide solution were simultaneously dropwise added into the carrier mixture solution under stirring for precipitation, during which the reaction solution was kept at pH 12. After the precipitation was completed, the reaction solution was heated to 100° C. for aging for 6 h, and filtrated to collect a filter cake, which was rinsed with deionized water to neutral, dried at 110° C. for 24 h and calcinated at 500° C. for 4 h to obtain a nano-Cu-based catalyst precursor 45CuO3ZnO4Ho$_2$O$_3$1Y$_2$O$_3$/42SiO$_2$5SnO$_2$. 1.56 g of zirconium tetra-n-propanol was dissolved in n-propanol with calculated amount, to which 10 g of the above catalyst precursor powder was added, impregnated at room temperature for 3 h, dried at 110° C. for 12 h, and calcinated at 600° C. for 4 h to obtain the surface modifier-coated nano-Cu-based catalyst (45CuO3ZnO4Ho$_2$O$_3$1Y$_2$O$_3$/42SiO$_2$5SnO$_2$@2% ZrO$_2$).

2. Preparation of 1,3-Propanediol

The preparation of 1,3-propanediol in Example 5 was basically the same as that in Example 1, except that in Example 5, the hydrogenation was performed at a pressure of 12 MPa, and a concentration of the methyl 3-hydroxypropionate raw material was 95%.

3. Evaluation of Catalyst

After the hydrogenation reaction was performed for 60 h, the hydrogenated product was analyzed qualitatively and quantitatively by gas chromatography, and results were as follows: the conversion rate of methyl 3-hydroxypropionate was 99.8%, the 1,3-propanediol selectivity was 90.1%, and a space-time yield of 1,3-propanediol was 0.164 g/(g·h)).

Example 6

1. Preparation of a Surface Modifier-Coated Cu-Based Nano-Catalyst 54.70 g of copper nitrate, 10.96 g of zinc nitrate and 1.95 g of indium nitrate were dissolved in 533 mL of deionized water to form a mixed nitrate solution. 25 g of silica sol, 0.6 g of SnO$_2$ nano-powder, 12.5 mL of ionized water and 8.5 g of glucose were added to a reactor, cooled to 10° C. and kept at 10° C. to form a carrier mixture solution. The mixed nitrate solution and a 4 mol/L sodium hydroxide solution were simultaneously dropwise added into the carrier mixture solution under stirring for precipitation, during which the reaction solution was kept at pH 11. After the precipitation was completed, the reaction solution was heated to 90° C. for aging for 4 h. After the aging was completed, the reaction solution was filtered to collect a filter cake, which was rinsed with deionized water to neutral, dried at 120° C. for 24 h and calcinated at 400° C. for 4 h to obtain a nano-Cu-based catalyst precursor 60CuO10ZnO3In$_2$O$_3$/25SiO$_2$2SnO$_2$. 1.23 g of aluminum sec-butoxide was dissolved in sec-butanol with calculated amount, to which 10 g of the above catalyst precursor powder was added, impregnated at room temperature for 3 h, dried at 110° C. for 12 h, and calcinated at 600° C. for 4 h to obtain the surface modifier-coated nano-Cu-based catalyst (60CuO10ZnO3In$_2$O$_3$/25SiO$_2$2SnO$_2$@3% Al$_2$O$_3$).

2. Preparation of 1,3-Propanediol

The preparation of 1,3-propanediol in Example 6 was basically the same as that in Example 1, except that in Example 6, the hydrogenation was performed at 160° C. and a pressure of 8.0 MPa.

3. Evaluation of Catalyst

After the hydrogenation reaction was performed for 60 h, the hydrogenated product was analyzed qualitatively and quantitatively by gas chromatography, and results were as follows: the conversion rate of methyl 3-hydroxypropionate was 99.2%, the 1,3-propanediol selectivity was 86.5%, and a space-time yield of 1,3-propanediol was 0.157 g/(g·h)).

Example 7

1. Preparation of a Surface Modifier-Coated Cu-Based Nano-Catalyst 59.26 g of copper nitrate, 1.95 g of indium nitrate and 1.2 g of germanium dioxide nanoparticles were dissolved in 497 mL of deionized water to form a mixed nitrate solution. 26 g of silica sol, 0.6 g of SnO$_2$ nano-powder, 12.5 mL of ionized water and 8.5 g of glucose were added to a reactor, cooled to 0° C. and kept at 0° C. to form a carrier mixture solution. The mixed nitrate solution and a 4 mol/L sodium hydroxide solution were simultaneously dropwise added into the carrier mixture solution under stirring for precipitation, during which the reaction solution was kept at pH 11. After the precipitation was completed, the reaction solution was heated to 90° C. for aging for 4 h, and filtrated to collect a filter cake, which was rinsed with deionized water to neutral, dried at 110° C. for 24 h and calcinated at 500° C. for 4 h to obtain a nano-Cu-based catalyst precursor 65CuO3In$_2$O$_3$4GeO$_2$/26SiO$_2$2SnO$_2$. 0.82 g of aluminum sec-butoxide was dissolved in sec-butanol with calculated amount, to which 10 g of the above catalyst precursor was added, impregnated at room temperature for 3 h, dried at 90° C. for 12 h, and calcinated at 600° C. for 4 h to obtain the surface modifier-coated nano-Cu-based catalyst (65CuO3In$_2$O$_3$4GeO$_2$/26SiO$_2$2SnO$_2$@2% Al$_2$O$_3$).

2. Preparation of 1,3-propanediol

The preparation of 1,3-propanediol in Example 7 was basically the same as that in Example 1, except that in Example 6, the hydrogenation was performed at a pressure of 10.0 MPa, and the ratio of hydrogen to methyl 3-hydroxypropionate was 30:1.

3. Evaluation of Catalyst

After the hydrogenation reaction was performed for 60 h, the hydrogenated product was analyzed qualitatively and quantitatively by gas chromatography, and results were as follows: the conversion rate of methyl 3-hydroxypropionate was 99.1%, the 1,3-propanediol selectivity was 80.5%, and a space-time yield of 1,3-propanediol was 0.146 g/(g·h)).

Comparative Example 1

The preparation of the Cu-based nano-catalyst (53CuO4ZnO3Ho$_2$O$_3$3In$_2$O$_3$/32SiO$_2$5SnO$_2$) in Comparative Example 1 was basically the same as that in Example 1, except that the catalyst was not subjected to surface modification. The preparation of 1,3-propanediol and the evaluation of catalyst in Comparative Example 1 were the same as that in Example 1, and the results were as follows. An initial conversion of methyl 3-hydroxypropionate and an initial 1,3-propanediol selectivity were 98.7% and 82.4%, respectively. After reaction for 200 h, the conversion of methyl 3-hydroxypropionate and the 1,3-propanediol selectivity decreased to 91.2% and 74.8%, respectively.

Comparing the evaluation results of the catalyst of Example 1 and Comparative Example 1, it revealed that the catalyst with surface modification exhibited more excellent hydrogenation activity, selectivity and stability on methyl 3-hydroxypropionate. The main reason was that the coating of surface modifier on the surface of the catalyst formed more oxygen vacancies on the surface of the catalyst, which enhanced the adsorption and activation ability of the catalyst to the ester carbonyl, and the coating effectively inhibited the sintering of the active copper species and the loss of the silica carrier, which significantly enhanced the long-life stability of the catalyst.

Comparative Example 2

The surface modifier-coated Cu-based nano-catalyst ($53CuO_4ZnO3Ho_2O_33In_2O_3/32SiO_25SnO_2@1\%$ $Al_2O_3$) prepared in Example 1 was adopted herein. The preparation of 1,3-propanediol was basically the same as that in Example 1, except that the raw material in Comparative Example 2 was a 20 wt. % methyl 3-hydroxypropionate methanol solution. The catalyst evaluation conditions were the same as that of Example 1, and the experimental results were as follows. The conversion of methyl 3-hydroxypropionate was 98.4%, and the 1,3-propanediol selectivity was 85.4%. After reaction for 500 h, the conversion of methyl 3-hydroxypropionate and the 1,3-propanediol selectivity decreased to 90.8% and 80.1%, respectively.

Comparing the evaluation results of the catalyst of Example 1 and Comparative Example 2, it revealed that the use of a high-concentration methyl 3-hydroxypropionate could significantly prolong the service life of the catalyst, mainly due to the fact that the high-concentration raw material could mitigate structural damage to the catalyst caused by the flushing with a large amount of solvent.

Comparative Example 3

The preparation of the surface modifier-coated Cu-based nano-catalyst ($53CuO_4ZnO3Ho_2O_33In_2O_3/32SiO_25SnO_2@1\%$ $Al_2O_3$) in Comparative Example 3 was basically the same as that in Example 1, except for that the carrier mixture solution in Comparative Example 3 was formed and kept at 50° C. for precipitation. The preparation of 1,3-propanediol and catalyst evaluation conditions were the same as that in Example 1, and the experimental results were as follows. The conversion of methyl 3-hydroxypropionate was 85.4%, and the 1,3-propanediol selectivity was 78.6%.

Comparing the evaluation results of the catalyst of Example 1 and Comparative Example 3, it revealed that the catalyst prepared by low-temperature precipitation had a higher dispersion of active component particles and additive components particles, resulting in higher hydrogenation activity and selectivity.

Comparative Example 4

The preparation of the surface modifier-coated Cu-based nano-catalyst in Comparative Example 4 was basically the same as that in Example 1, except that the surface modifier used in Comparative Example 4 was different from that in Example 1, and the results were shown in Table 1.

TABLE 1

Hydrogenation performance of Cu-based nano-catalysts coated with different surface modifiers

| Surface modifier | Conversion of 3-HPM (%) | 1,3-PDO selectivity (%) |
| --- | --- | --- |
| Aluminum nitrate | 77.9 | 92.6 |
| Zirconium nitrate | 66.2 | 85.4 |
| Zinc nitrate | 66.2 | 85.4 |
| Manganese nitrate | 69.3 | 84.5 |
| Sucrose | 82.5 | 86.5 |
| Propyltrimethoxysilane | 91.3 | 87.9 |

As could be seen from Table 1, when preparing 1,3-propanediol via hydrogenation of methyl 3-hydroxypropionate using Cu-based nano-catalysts coated with different surface modifiers, these catalysts showed poorer performance in terms of the hydrogenation conversion and the selectivity of the target product than the Cu-based nano-catalyst coated with the surface modifier in Example 1.

The foregoing are only preferred embodiments of the present disclosure and are not intended to limit the present disclosure. Any modifications, equivalent substitutions, and improvements made within the spirit and principles of the present disclosure shall be included in the scope of protection of the present disclosure.

What is claimed is:

1. A method for preparing 1,3-propanediol, comprising:
   pumping, by a feed pump, a methyl 3-hydroxypropionate solution into a tubular fixed-bed reactor for hydrogenation to obtain a reaction mixture, wherein the tubular fixed-bed reactor is loaded with a surface modifier-coated nano-Cu-based catalyst; a concentration of methyl 3-hydroxypropionate in the methyl 3-hydroxypropionate solution is 90-99 wt. %; and the nano-Cu-based catalyst comprises an active component, an additive component, and a carrier, wherein the active component is Cu, and the additive component is a metal oxide of $XO_{n/2}$, wherein a metal in the metal oxide is represented by X;
   subjecting the reaction mixture to rectification to separate light components from heavy components, wherein the light components comprise methanol, n-propanol, methyl propionate, methyl 3-hydroxypropionate and 1,3-propanediol; and the heavy components comprise 1,3-propanediol mono-propionate and 1,3-propanediol mono-3-hydroxypropionate; and
   feeding the heavy components back to the tubular fixed-bed reactor for secondary hydrogenation; and subjecting the light components to separation to collect 1,3-propanediol;
   wherein the surface modifier-coated nano-Cu-based catalyst is prepared through steps of:
   (1) mixing a copper precursor and an $X^{n+}$ precursor in a preset weight ratio to form a mixed aqueous solution with a molar concentration of 0.1-1 mol/L;
   (2) preparing a base solution with a molar concentration of 0.5-5 mol/L as precipitant;
   (3) adding a sol or nano-powder of $SiO_2$ and $SnO_2$ to a cooled aqueous solution containing an organic polyol to form a carrier mixture solution;
   (4) simultaneously adding the mixed aqueous solution and the base solution to the carrier mixture solution under stirring for co-precipitation to form a slurry, wherein a pH of the slurry is kept at 10-12 during the co-precipitation;
   (5) after the co-precipitation is completed, heating the slurry to 80-100° C. for aging for 2-24 h, followed by filtration, washing, atmospheric-pressure drying, and calcination to obtain a nano-Cu-based catalyst precursor;
   (6) subjecting the nano-Cu-based catalyst precursor to impregnation with a surface modifier, drying and calcination to obtain a catalyst powder; and
   (7) subjecting the catalyst powder obtained from step (6) to pressing-sieving or extrusion, and reduction activation to obtain the surface modifier-coated nano-Cu-based catalyst;
   wherein the surface modifier is selected from the group consisting of an organic aluminum salt, an organic zirconium salt and a combination thereof;

the base solution is one or two of sodium hydroxide, sodium bicarbonate, sodium carbonate, ammonium carbonate, ammonium bicarbonate and ammonia;

the carrier is a $SiO_2$—$SnO_2$ composite; and

X is selected from the group consisting of Zn, Ga, Ge, In, Y, Ce, Ho and a combination thereof.

2. The method of claim 1, wherein the surface modifier is aluminum isopropoxide, aluminum sec-butoxide, zirconium n-propoxide, zirconium n-butoxide, or a combination of one of aluminum isopropoxide and aluminum sec-butoxide and one of zirconium n-propoxide and zirconium n-butoxide.

3. The method of claim 1, wherein the surface modifier-coated nano-Cu-based catalyst comprises 30-70 wt. % of the active component, 1-15 wt. % of the additive component, 15-60 wt. % of $SiO_2$, 1-5 wt. % of $SnO_2$, and 0.3-9 wt. % of the surface modifier.

4. The method of claim 1, wherein the co-precipitation in step (4) is performed at a temperature ranging from $-10°$ C. to $10°$ C.

5. The method of claim 1, wherein operation parameters of the tubular fixed-bed reactor are as follows: a temperature at a constant-temperature section is 160-200° C., pressure is 8-12 MPa, the concentration of the methyl 3-hydroxypropionate solution is 90-99 wt. %, a hydrogen-to-methyl 3-hydroxypropionate molar ratio is 30-200:1, and a weight hourly space velocity is 0.2-0.6 $h^{-1}$.

\* \* \* \* \*